(12) United States Patent
Takashima et al.

(10) Patent No.: US 8,227,360 B2
(45) Date of Patent: Jul. 24, 2012

(54) SHEET FOR USE AS FILTER, MASK OR THE LIKE HAVING BACTERIA ADSORBING FUNCTION

(76) Inventors: Seisuke Takashima, Kurasiki (JP); Masatoshi Iida, Shimotugagun (JP)

(*) Notice: Subject to any disclaimer, the term of this patent is extended or adjusted under 35 U.S.C. 154(b) by 425 days.

(21) Appl. No.: 11/666,658

(22) PCT Filed: Oct. 20, 2005

(86) PCT No.: PCT/JP2005/019743
§ 371 (c)(1),
(2), (4) Date: Jul. 17, 2008

(87) PCT Pub. No.: WO2006/049067
PCT Pub. Date: May 11, 2006

(65) Prior Publication Data
US 2009/0117798 A1    May 7, 2009

(30) Foreign Application Priority Data

Nov. 2, 2004  (JP) .................. 2004-318659
Dec. 10, 2004 (JP) .................. 2004-357574

(51) Int. Cl.
*B32B 27/14* (2006.01)
(52) U.S. Cl. .......................... 442/69; 442/123
(58) Field of Classification Search .......... 442/69, 442/123
See application file for complete search history.

(56) References Cited

FOREIGN PATENT DOCUMENTS

| JP | 62288076 | * | 12/1987 |
| JP | 1991-328526 | * | 1/1990 |
| JP | 10-8376 A | | 1/1998 |
| JP | 10-25663 A | | 1/1998 |
| JP | 2001-377311 | * | 7/1999 |
| JP | 2003-342871 A | | 12/2003 |

OTHER PUBLICATIONS

International Search Report of PCT/JP2005/019743, date of mailing Feb. 28, 2006.

* cited by examiner

*Primary Examiner* — Lynda Salvatore
(74) *Attorney, Agent, or Firm* — Westerman, Hattori, Daniels & Adrian, LLP

(57) ABSTRACT

[Problem to be Solved]
A sheet made of a fabric or paper coated with a substance which has a strong function to adsorb, remove and make harmless microbes such as bacteria and viruses is to be configured so as to be usable as a filter, a mask or the like capable of removing the microbes such as the bacteria and viruses.

[Solving Means]
A sheet made of a fabric which uses a fibrous material, for example, polyester in which a sulfenate group or a carboxylate group has been introduced, and has a surface coated, for example, with anatase type titanium oxide makes microbes such as bacteria and viruses harmless by adsorbing these microbes and has sufficient air permeability, therefore being usable as a filter, a mask or the like. Furthermore, a sheet made of a fabric or paper which is impregnated with an aqueous solution of polyvinyl alcohol copolymerized with a monomer having a sulfonate group or carboxylate group as a fabric size and on which titanium oxide is coated and fixed has a function to make harmful microbes harmless by adsorbing these microbes, therefore being usable not only as a filter or a mask but also as fruit packing material or the like.

1 Claim, 2 Drawing Sheets

SHEET FOR USE AS FILTER, MASK OR THE LIKE HAVING BACTERIA ADSORBING FUNCTION

TECHNICAL FIELD

The present invention relates to a sheet which is made of a fabric or paper and to be used as a filter, a mask or the like in a ventilation equipment for cleaning indoor air in houses, office buildings and the like goods, and a sheet which is made of paper and to be used as wallpaper, fruit packing for insect prevention during cultivation or the like.

PRIOR ART

Conventional ventilation equipments are configured to clean indoor air by exchanging indoor air with external air. The conventional ventilation equipments therefore use nearly no filter but uses sheets which have main functions to remove dusts and the like contained in the external air. Furthermore, there has been scarcely known a mask which has a bacteria adsorbing function. Furthermore, esthetic factors have been preferred for wallpaper which is to be use indoors and there is known no wallpaper for which an antifungal property and a bacteria adsorbing function are considered. Moreover, speaking of sheets to be used in an agricultural field, materials for packing fruits and the like goods, in particular, sheets are used only for preventing fruit surfaces from physical damages and nearly no measure is taken for prevention of propagation of microbes and decomposition of fruits.

In recent years, in particular, measures have been required for pathogenic viruses such as corona virus and influenza virus which often break out diseases.

On the other hand, the inventor developed a composite filter for purifying water and applied the filter as PCT/JP02/13239. This application was thereafter internationally published (patent literature 1). Ion exchanging resin is effective for inactivation of viruses and pathogenic bacteria as described in the specification of the patent.

Furthermore, a nonwoven fabric is capable of adsorbing and removing bacteria such as a cholera bacillus, a dysentery bacillus and an anthrax bacillus. Out of contents of the above mentioned specification, the inactivation of the bacteria with the ion exchange resin and adsorption of the bacteria with the nonwoven fabric are described in non-patent literatures 1 and 2 respectively mentioned below.

[Patent Literature I] WO 03/053868 AI
[Non-patent Literature 1] Magazine of Japan Medical instrument academic circle 56: 499, 1986
[Non-patent Literature 2] Magazine of Japan artificial organ academic circle 18: 1372, 1989

A possibility is therefore considered to realize removal and inactivation of bacteria in air using the ion exchanging resin, the nonwoven fabric or a combination of the ion exchanging resin and the nonwoven fabric. It is therefore possible to clean indoor air, and prevent infection of bacteria and viruses in particular, by disposing the ion exchange resin or the nonwoven fabric in a ventilation equipment of a building.

When the ion exchanging resin is to be used as a filter, however, the ion exchanging resin which generally has a particle form and is packed in a container can hardly have a simple form and requires inconvenient handling. It is difficult in particular to configure the ion exchanging resin so as to have a planar form like paper or cloth which can easily be disposed at any location and exchanged in an occasion where a cleaning function is degraded or a similar occasion.

Furthermore, it is difficult to obtain a sufficient infection preventive effect by the inactivation of the bacteria and the viruses only with the nonwoven fabric which is capable of removing the dusts.

The inventor developed a filter having a simple form like cloth which can easily be disposed and exchanged, for example, in a ventilation equipment and is capable of inactivating the bacteria, the viruses or the other microorganism in air, and applied the filter as an application laid open No. 2003-195591.

The filter according to this application is manufactured by dipping a nonwoven fabric into a 1 to 10% aqueous solution of a substance such as a sulfate type or sulfoxylate type surface active agent which has a function to inactivate bacteria, viruses and the like which is mixed with 1 to 10% aqueous solution of polyvinyl alcohol denatured with carboxylic acid (hereinafter abbreviated as CA-PVA) as a fabric size, and then fixing the fabric size by heating the nonwoven fabric.

The bacteria inactivating filter according to this application uses ion exchange resin for inactivating the bacteria as described above but cannot provide a sufficient bacteria inactivating effect unless the ion exchanging rein is used in a relatively large amount.

The filter therefore requires coating the nonwoven fabric with a large amount of the ion exchanging resin and fixing the ion exchanging resin, and since the ion exchange resin has a particulate or granular form, the filter requires coating further with the ion exchanging resin after dipping the fabric into the fabric size and further heating the fabric for fixing the ion exchanging resin to the fabric, thereby having a defect to require a long time and a high coat for manufacturing.

Furthermore, since the nonwoven fabric is coated with the ion exchanging resin in a large amount and allows no sufficient air circulation, more or less improvement is desired for the nonwoven fabric for use as a bacteria removing filter at a ventilating location or a mask.

Furthermore, the above described filter or the like which uses the ion exchangeing resin fixed on the nonwoven fabric is problematic also from a viewpoint of a manufacturing cost.

When the filter is used in a ventilation equipment, for example, the filter must be exchanged when a bacteria inactivating function or the like is degraded. It is therefore desirable that a filter can be manufactured at a cost as low as possible. It is therefore also desired to configure a paper sheet so as to have an antifungal property or a bacteria inactivating function.

Furthermore, there are used many disposable masks which are made of paper. It is extremely desirable to realize a mask which is made of paper and has an antifungal property or a bacteria inactivating function.

For reasons described above, it is desired to realize a sheet which is made of paper and has an antifungal property or a bacteria inactivating function.

Furthermore, a sheet which is made of paper and has an antifungal property or a bacteria inactivating function will be utilizable in many ways other than the above described filter and mask. The sheet will be usable, for example, as paper for indoor use such a wall paper and fruit packing paper, thereby providing various effects.

DISCLOSURE OF THE INVENTION

[Problems to be Solved by the Invention]

The present invention provides a sheet made of a fabric which uses a substance having strong functions for adsorbing, moreover removing and making harmless microbes such as bacteria and viruses, provides a sufficient bacteria removing function even when a material fiber is coated with the substance in a small amount and maintains sufficient air permeability, thereby being optimum for use as a filter in a ventilation equipment or a mask.

Furthermore, the present invention provides a sheet made of paper which is usable not only as the above described filter or mask but also as packing paper which has a moisture retention, an antifungal property and a bacteria removing function for maintaining tastes and freshness of fruits.

[Means for Solving the Problems]

The sheet made of the fabric according to the present invention uses a fibrous material copolymerized or blended with a substance having a sulfonate group, a carboxylate group or a sulfate group and is characterized in that titanium oxide is coated over a surface of the fabric.

Polyester is the most desirable as the fibrous material of the sheet made of the fabric according to the present invention, or it is desirable that the sheet made of the fabric according to the present invention uses as a material polyester into which sulfonic acid has been introduced and which is coated with titanium oxide.

However, the sheet of the fabric according to the present invention may use a material so far as the material contains polyester, for example, a material containing a mixture of nylon and polyester fibers or a mixture of cotton and polyester fibers. In other words, a fabric which uses the above described polyester into which sulfonate group has been introduced and titanium oxide sufficient bacteria removing function and is usable as a material of the sheet made of the fabric according to the present invention for use as a filter or a mask.

Like the sheet made of the fabric, a sheet made of paper according to the present invention is capable of allowing titanium oxide to adhere thereto by coating the sheet with titanium oxide when the sheet has been impregnated with an aqueous solution of alcohol copolymerized with a monomer having a sulfonate group or carboxylate group as a fabric size.

Furthermore, anatase type titanium oxide is most preferable as titanium oxide to be coated over the sheet made of the fabric according to the present invention.

Furthermore, a certain definite bacteria removing function can be obtained using alumina sintered at 400° C. or 1000° C. instead of the above described titanium oxide. Moreover, rutile type titanium oxide, amorphous type titanium oxide or the like has a certain definite bacteria removing function and is usable for sheet made of the fabric according to the present invention.

A bacteria removing effect is enhanced by irradiating the various kinds sheets made of fabrics according to the present invention with visible rays.

The sheet made of the fabric according to the present invention may be the above described sheet made of the fabric which has been irradiated with a visible ray and provides an enhanced effect.

Similarly, it is possible to enhance a bacteria removing function of the sheet made of paper according to the present invention by irradiating the sheet with a visible ray.

The above described sheet made of the fabric or paper according to the present invention has a high function to adsorb microbes and the like, and a function to inactivate adsorbed microbes as apparent from results of experiments described later.

In other words, a most importance point of the present invention lies in a point that an extremely interesting phenomenon has been found out on the basis of a method for simulating adsorption behaviors of bacteria or viruses, thereby making it possible to adsorb the bacteria or viruses.

Surfaces of the bacteria are composed of glycolipids and proteins as is generally known.

Albumin which has a clear chemical constitution and is free from water-soluble sugar chain (albumin in beef serum, molecular weight: 67,000) was selected as a model for evaluation of a capability of fabric to adsorb bacteria and viruses since a glycolipid which has a large molecular weight has a difficult point that the glycolipid is hardly soluble in water and allows the capability to be evaluated only in a low concentration range.

As a result of examinations using albumin, there was obtained data which allowed to estimate a bacteria removing function such as a microbe inactivating function of the sheet made of the fabric according to the present invention, thereby clarifying that the sheet made of the fabric according to the present invention is capable of accomplishing the object of the present invention.

The sheet made of paper according to the present invention can also accomplish the object since a similar result was obtained of the sheet made of paper according to the present invention.

[Effect of the Invention]

The sheet made of the fabric or paper according to the present invention has a strong function to adsorb bacteria, viruses or other microbes, and exhibits an effect to inactivate the adsorbed microbes.

BEST MODE FOR CARRYING OUT THE INVENTION

A most desirable sheet made of a fabric according to the present invention uses a fibrous material composed of polyester as a main body into which sulfonic acid has been introduced, coated with titanium oxide or the like and irradiated with visible rays such as natural rays, and has a function to adsorb and remove microbes contained in air, for example, when used as a filter in a ventilation equipment or the like as described above.

When paper is used instead of the fabric as a material, it is difficult to introduce a sulfonate group or a carboxylate group.

The sheet made of the paper according to the present invention is impregnated with vinyl alcohol copolymerized with a monomer having a sulfonate group or a carboxylate group as a fabric size to fix titanium oxide as described above.

The above described function of the sheet made of the fabric according to the present invention will be described below on the basis of experiments carried out using albumin.

First, detailed description will be made of a reason why the experiments were carried out using albumin. The inventor designed instruments on the basis of knowledge which has so far been obtained by examining agents to adsorb and remove viruses and pathogenic substance out of blood. Speaking concretely, the inventor has clarified that cation exchange resin (activation point; sulfonic acid) and silica/alumina exhibit high adsorption activities for hepatitis B antigen and acquired immune deficiency syndrome virus, and that polyester denatured by sulfonic acid is effective for inactivation of cedar pollinosis antigen.

Out of proteins, lipids and glucides which compose surface of microbes, proteins have polarities and high molecular weights.

Accordingly, myoglobin (molecular weight: 14,000), ovoalbumin (molecular weight: 33,000) and albumin (molecular weight: 67,000) were selected as models of microbes which were pathogenic substances. Out of these models, an absorption spectrum method in an ultraviolet region which has high sensitivity is not applicable to myoglobin which is brownish and whose aqueous solution is also colored. Albumin was therefore considered adequate for simulation of influences due to adsorbents on proteins on the surfaces of the microbes and selected as a model of the pathogenic substances since a substance having a molecular weight as large as possible causes stronger molecular interlocking and albumin has known amino acid composition and physical properties.

For reasons described above, the sheet made of the fabric according to the present invention has been developed on the basis of results obtained by experiments which are described below, and a method for the experiments and obtained results will be described below:

(A) Fabrics and Model Substances (Adsorbents) used for the Experiments

The fabrics used for the experiments were fabrics mentioned in (i) below which contained the substances used in the filter described in the above-mentioned application and adsorbed adsorbents listed in (ii) below.

(i) a. polyester (standard cloth),
  b. cotton (standard cloth),
  c. nylon (standard cloth),
  d. polyester (2.5 mol % of polyester prepared by Kurashiki Rayon into which sulfonic group was introduced),
  e. commercially available paper, each fabric was used in a size 10 mm×10 mm.

In addition, the above-mentioned polyester prepared by Kuraray Co. Rayon is made of polyester fiber, Giant Up by trade name, which is span while mixing a stock solution of polyester with titanium oxide.

(ii) a. Cation exchange resin ($SO_3H$ type),
  b. alumina (calcined at 400° C.),
  c. alumina (calcined at 1000° C.),
  d. titanium oxide (anatase type),
  e. titanium oxide (rutile type),
  f. titanium oxide (amorphous)

(B) Method for Experiments

The fabric or a predetermined weight (1.0 to 100.0 mg) of the absorbent was dipped in an aqueous solution of albumin and a concentration was measured 30 minutes later.

In case of experiments which used the adsorbents out of the experiments, a document solution was allowed to permeate through a disposable filter (diameter 0.45 μm) and absorbance was measured at a wavelength of 278 nm before measuring concentrations of albumin. From the specral absorbance measured at 278 nm, reactivities of the fabrics and the adsorbents on albumin were evaluated as parameters of rates of change relative to original concentrations.

In other words, a rate of reaction is determined as follows:

Reaction ratio of albumin=$(A_n-A)/A_0$ wherein $A_0$ represents absorbance of an aqueous solution of albumin before a reaction and A designates absorbance of the aqueous solution of albumin after the reaction.

Furthermore, three sheets of a fabric containing sulfonic groups introduced at 2.5 mol % and cut in a size of 10 mm×10 mm were dipped in an aqueous solution of albumin at 100.0 ppm filled in a test tube made of quartz, the test tube was tightly closed with a silicone rubber stopper and exposed to sunlight for 1, 2, and 3 hours, whereafter rates of change of albumin were measured. On the other hand, only the aqueous solution of albumin was exposed for 3 hours.

Furthermore, anatase type titanium oxide was sampled in amounts of 1.0 mg, 2.0 mg and 3.0 mg as titanium oxide, dipped into an aqueous solution of albumin at 100 ppm, enclosed into test tubes made of quartz and irradiated for 1 hour right under lamps emitting a monochromatic ray at 423 nm. For this experiment also, only 5.0 ml of an aqueous solution of albumin was irradiated with the ray for 1 hour as a reference test.

Results obtained by the above described experiments will be described on the basis of FIGS. 1, 2 and 3.

The following table 1 lists rates of change of albumin in various kinds of fibrous materials: (A) being cases of a single sheet of fibrous material and (B) being cases of three sheets of fibrous material.

TABLE 1

(A)

| Sample (single sheet) | Reaction ratio of albumin |
| --- | --- |
| a. polyester (standard) | 0.03 |
| b. cotton (standard) | 0.02 |
| c. nylon (standard) | 0.08 |
| d. polyester (prepared by Kuraray Co.) | 0.12 |
| e. Commercially available paper (fruit packing material) | 0.01 |

(B)

| Sample (3 sheets) | Reaction ratio of albumin |
| --- | --- |
| a. polyester (standard) | 0.12 |
| b. cotton (standard) | 0.01 |
| c. nylon (standard) | 0.05 |
| d. polyester (prepared by Kurashiki Rayon) | 0.34 |
| e. commercially available paper (fruit packing material) | 0.02 |

Furthermore, the following table 2 lists rates of change of albumin after irradiating five sheets of polyester with sunlight for 0. 1, 2 and 3 hours.

TABLE 2

| Irradiation time | Reaction ratio of albumin |
| --- | --- |
| 0 hour | 0.49 |
| 1 hour | 0.56 |
| 2 hours | 0.62 |
| 3 hours | 0.61 |

Furthermore, the following table 3 lists rates of change of the cation exchanging resin mentioned as the conventional example.

TABLE 3

| Sample weight | Reaction ratio of albumin |
| --- | --- |
| 1.0 mg | 0.10 |
| 2.0 mg | 0.02 |
| 5.0 mg | 0.08 |
| 10.0 mg | 0.16 |

Furthermore, the following table 4 lists rates of change of albumin in alumina sintered at 400° C. and 1000° C. respectively.

TABLE 4

| | Reaction ratio of albumin | |
| --- | --- | --- |
| Sample weight | Alumina at 400° C. | Alumina at 1000° C. |
| 10 mg | 0.40 | 0.54 |
| 20 mg | 0.65 | 0.87 |
| 30 mg | 0.90 | 0.94 |

TABLE 4-continued

| | Reaction ratio of albumin | |
|---|---|---|
| Sample weight | Alumina at 400° C. | Alumina at 1000° C. |
| 50 mg | 0.93 | 0.32 |
| 100 mg | 0.96 | 0.92 |

Furthermore, the following table 5 lists rates of change of anatase oxide type albumin: Table 5 (A) showing rates of change of albumin irradiated with visible rays and Table 5 (B) showing rates of change of albumin not irradiated with the visible rays.

TABLE 5

| | Reaction ratio of albumin |
|---|---|
| (A) Sample weight | |
| 1.2 mg | 0.48 |
| 2.6 mg | 0.85 |
| 2.1 mg | 0.91 |
| (B) Sample weight | |
| 1.1 mg | 0.00 |
| 2.3 mg | 0.51 |
| 3.9 mg | 0.97 |

Furthermore, the following table 6 lists rates of change of albumin in rutile type titanium (A) and amorphous type albumin.

TABLE 6

| | Reaction ratio of albumin |
|---|---|
| (A) Sample weight | |
| 11.0 mg | 0.27 |
| 19.5 mg | 0.36 |
| 30.2 mg | 0.52 |
| 50.5 mg | 0.76 |
| 100.0 mg | 0.97 |
| (B) Sample weight | |
| 1.7 mg | 0.21 |
| 2.7 mg | 0.50 |
| 4.5 mg | 0.58 |
| 0.7 mg | 0.70 |

Moreover, FIGS. 1 and 2 show photocatalytic effects of polyester, polyester incorporated with anatase type titanium oxide and anatase type titanium oxide, and FIG. 3 shows albumin adsorption rates of titanium oxide.

As shown in these drawings, polyester which has been denatured by sulfonic acid and further incorporated with titanium oxide is active on albumin, whereas a fabric which is made only of polyester, cotton or nylon is inactive.

Speaking of albumin removing activities of the adsorbents (rates of change), anatase type titanium oxide exhibits the highest activity, rutile type titanium oxide has an activity on the order of $1/20$ of that of anatase type titanium oxide and amorphous titanium oxide has an activity approximately $1/2$ of the activity of anatase type titanium oxide as shown in FIG. 3.

Furthermore, the cation exchange resin (sulfonic acid type) exhibited a reaction ratio of albumin which was not so high as shown in Table 3.

Furthermore, alumina exhibited a reaction ratio of albumin which was higher than that obtained with the cation exchange resin as shown in Table 4: an activity of the sample calcined at 400° C. ($\gamma$ type, acid) being a little higher than that of the sample calcined at 1000° C. ($\alpha$ type, neutral).

Further, as apparent from Table 5, it was recognized that an albumin removing activity of anatase type titanium oxide is remarkably enhanced by irradiating anatase type titanium oxide with a visible ray (monochromatic ray at 423 nm). In addition, an ultraviolet absorption spectrum of anatase type titanium oxide was also remarkably changed, or absorption became faint at maximum absorption wavelengths of 275 to 278 nm on a spectrum of the original aqueous solution of albumin and broad absorption peaks appeared in the vicinities of 250 nm and 320 nm as shown in FIG. 2.

Furthermore, since an optimum concentration is important for analyzing behaviors of albumin at a high sensitivity from spectra, 100 ppm was selected.

Next, speaking of albumin removing capabilities of the three kinds of standard fabrics shown in Table 1, these fabrics have low albumin removing capabilities on the order of 2% to 8% as exemplified by cotton having a capability of 2% and nylon having a capability of 8%. Furthermore, the albumin adsorbing-removing capabilities cannot be enhanced even when each fabric is used in a larger number of three sheets.

Furthermore, a result obtained by carrying out a similar measurement using commercially available paper is shown on line e in Table 1.

On the other hand, the fabric which uses polyester denatured by sulfonic acid as a material exhibits an albumin adsorbing-removing rate of 12% even when this fabric is used in a single sheet or a rate of 34% approximately three times as high when the fabric is used in three sheets. Furthermore, it is considered that a fiber of polyester denatured by sulfonic acid exhibits an optical deodorizing capability. A rate of change of albumin was enhanced approximately 30% or so as shown in Table 2 when an aqueous solution of albumin and five sheets of a fabric which was considered as having a deodorizing capability were put into a test tube made of quartz, the test rube was tightly closed and irradiated with natural light for 1, 2 and 3 hours.

Though the reaction ratio of albumin was enhanced by a photocatalytic function of titanium oxide incorporated in the fabric, it is considered that a main activity of this fabric on albumin is due to a copolymerized sulfonic group.

Next, description will be made of a method for forming sheet made of the fabric according to the present invention, concretely of a method for allowing titanium oxide to be carried by a fabric base.

After anatase type titanium oxide having particle diameters of 40 to 100 mesh, desirably 60 to 80 mesh, was suspended in an aqueous solution at 1% by weight of polyvinyl alcohol denatured by cation and polyacrylic acid so that the titanium oxide was 0.05 to 2.00% by weight of a fabric base, the fabric base was dipped in the suspension and dried at room temperature. When the fabric base is water repellent like polyester or nylon, a work can be facilitated by adding a trace amount of sulfonic acid type surface active agent. Though a material of the fabric base may be either a natural fiber or an artificial fiber, it is optimum to select a cloth which has interstices as fine as possible, for example, a fabric made of an extremely thin threads for cleaning spectacle lenses in order to effectively intercept fine particles floating in air from reaching man's trachea.

Furthermore, titanium oxide may be carried by coating a surface of a fabric base using a brush or the like.

Furthermore, not only anatase type titanium oxide but also rutile type titanium or $\gamma$ type alumina can be carried on a fabric base by a similar method.

Moreover, the sheet made of paper according to the present invention is manufactured by a method which is described below.

An aqueous solution of polyvinyl alcohol copolymerized with a monomer having a sulfonic group or a carboxylic group is used as a fabric size. The sheet made of paper according to the present invention can be manufactured by impregnating adequate paper with this fabric size and coating the paper with titanium oxide, thereby fixing titanium oxide to the paper.

The sheet made of fabric according to the present invention can be manufactured by similarity impregnating a fabric with the above described fabric size and fixing titanium oxide to the fabric.

The adsorbents such as titanium oxide used on the sheet made of fabric or paper according to the present invention has an antifungal function or a bacteria removing function as apparent from the above described experiments.

Furthermore, the sheet made of either fabric or paper according to the present invention which has the antifungal function or the bacteria removing function as apparent from the above described experiments is therefore usable as extremely an effective filter in a ventilation equipment or a mask.

Furthermore, the sheet made of paper according to the present invention is effective for removing indoor bacteria when used as wallpaper or the like. Moreover, the sheet made of paper according to the present invention is usable as fruit packing paper or the like which is capable not only of maintaining moisture of fruits but also of preventing influences on the fruits due to external microbes such as viruses and bacteria by removing and inactivating these microbes. In this case, it is possible to directly prevent the influences on fruit surfaces due to the above described microbes by disposing the sheet so that a surface on which the adsorbent such as titanium oxide is coated and fixed faces the fruit surfaces.

Furthermore, when the sheet made of paper according to the present invention is colored or has a function to cut off visible rays, rays of 400 nm to 500 nm in particular, the sheet is capable of preventing fruits from being discolored.

[Industrial Utility]

The sheet made of fabric according to the present invention is capable of adsorbing and inactivating, or sterilizing and making harmless, microbes such as bacteria or viruses owing to the adsorbent such as titanium oxide coated on a fibrous material used as a basic material and cloth. Furthermore, the adsorbent even in a small amount exhibits a remarkable effect to inactivate the microbes and the sheet made of fabric has sufficient air permeability.

The sheet made of fabric according to the present invention is usable as a filter in a ventilation equipment or a mask or the like.

Furthermore, the sheet made of paper according to the present invention also has an antifungal function and the like, therefore being usable as a filer or a mask. In addition, the sheet made of paper according to the present invention is usable not only as a paper product for indoor use such as wallpaper which provides an effect to clean indoor air but also fruit packing paper or the like which prevents insects during cultivation and can maintain qualities of fruits and the like for a long period of time.

Figure 1:
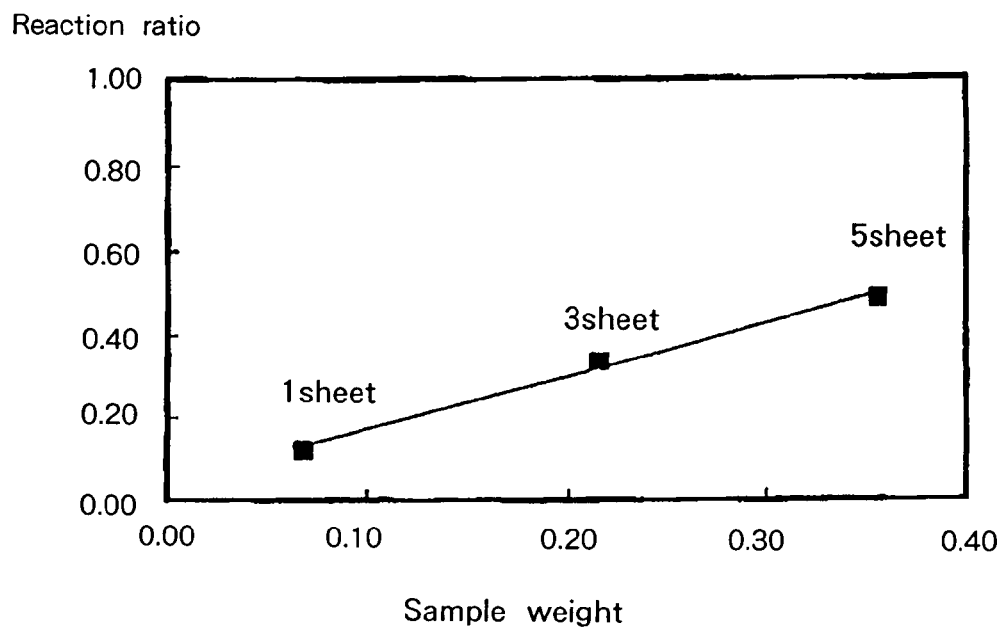
FIG. 1 is a graph showing a rate of reaction of albumin versus weights of polyester prepared by Kuraray Co. Rayon.
Figure 2:
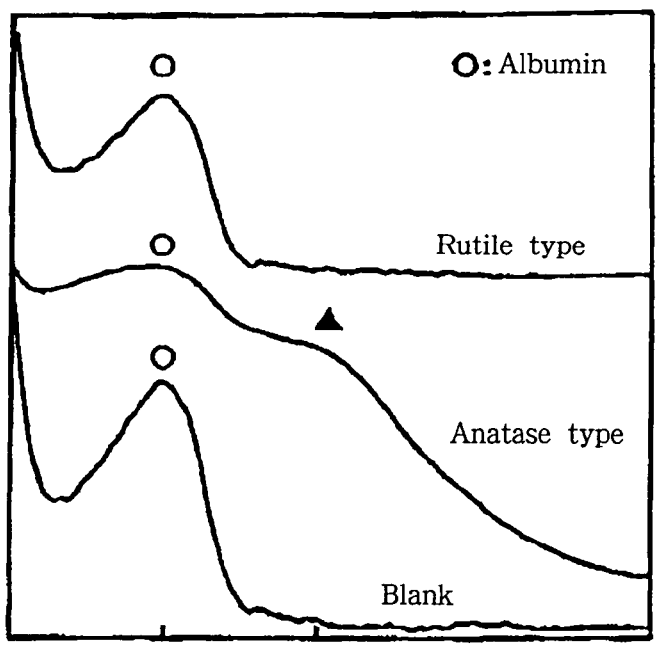
FIG. 2 shows ultraviolet absorption spectra of albumin in contact with titanium oxide.
Figure 3:
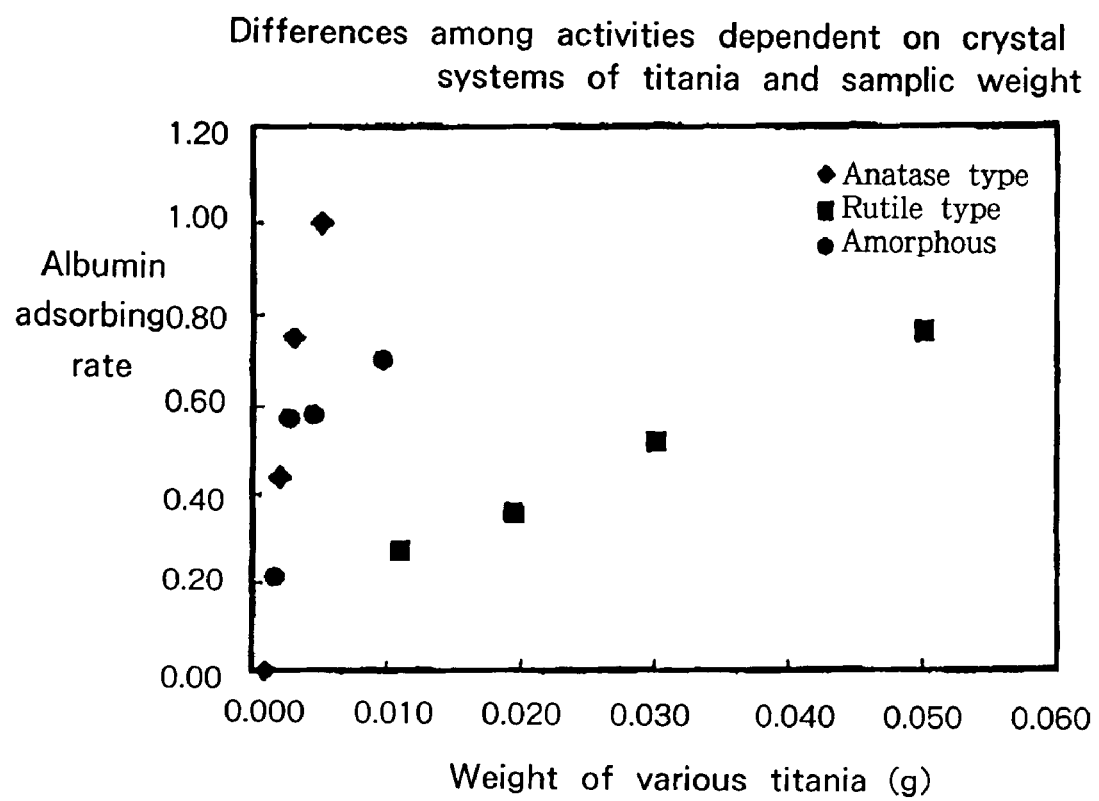
FIG. 3 is a diagram showing an albumin adsorbing rate versus weight of titanium oxide.

The invention claimed is:

1. A filter, comprising a breathable sheet of fabric or paper, the fabric or paper being impregnated with a paste of an aqueous solution of polyvinyl alcohol copolymerized with a monomer having a sulfonate group or a carboxylate group as a fabric size, wherein titanium oxide is affixed to the fabric or paper with the paste, and wherein the paste provides deodorizing and antibacterial properties.

* * * * *